United States Patent [19]

Ruggirello et al.

[11] Patent Number: 4,944,781
[45] Date of Patent: Jul. 31, 1990

[54] GAS CHROMATOGRAPH/AUTOSAMPLER COUPLING ASSEMBLY

[75] Inventors: Donald A. Ruggirello, Sunrise; Christopher R. Banfield, Plantation, both of Fla.

[73] Assignee: Schering Corporation, Kenilworth, N.J.

[21] Appl. No.: 378,745

[22] Filed: Jul. 12, 1989

[51] Int. Cl.⁵ .................... B01D 53/02; G01N 30/88
[52] U.S. Cl. ......................................... 55/386; 55/67; 73/23.41
[58] Field of Search ............... 55/67, 197, 386; 73/23.1

[56] References Cited

U.S. PATENT DOCUMENTS 4,044,593  8/1977  Haruki et al. ...................... 73/23.1
4,711,764  12/1987  Good ............................. 55/386 X

FOREIGN PATENT DOCUMENTS 1280471  12/1986  U.S.S.R. .......................... 73/23.1

OTHER PUBLICATIONS

Varian Vista 6000 Gas Chromatograph Manual.
Hewlett-Packard 7673A Autosampler Manual.
Varian Vista 402 Data System Manual.
Hewlett-Packard 3393A Integrator Manual.

Primary Examiner—Robert Spitzer
Attorney, Agent, or Firm—Anita W. Magatti; James R. Nelson; Stephen I. Miller

[57] ABSTRACT

An assembly for coupling a Hewlett-Packard Model HP 7673A autosampler mounted on a mounting plate to a Varian VISTA 6000 Model gas chromatograph having an injection site, includes a first bracket secured to the gas chromatograph on one side of the injection site and a second bracket secured to the gas chromatograph on the opposite side of the injection site, with the mounting plate secured to and mounted on the first and second brackets so as to permit access to the injection site by the autosampler; and securement screws for securing the mounting plate on the brackets.

25 Claims, 9 Drawing Sheets

GAS CHROMATOGRAPH/AUTOSAMPLER COUPLING ASSEMBLY

BACKGROUND OF THE INVENTION

This invention relates generally to gas chromatography, and more particularly, is directed to the automation of sample injections in a gas chromatograph.

Nitroglycerin assays are performed by gas chromatographic analysis of nitroglycerin in plasma, using electron capture detection. Originally, such nitroglycerin analyses were carried out using packed column gas chromatography. Recently, however, state of the art capillary gas chromatography has been used for such analyses.

When performing such nitroglycerin assays with state of the art gas chromatographs, it is generally required that the gas chromatograph provide a sensitivity which permits detection of the nitroglycerin to a level of 25 picograms/milliliter (pg/ml) of plasma. It has been found that the VISTA 6000 model gas chromatograph sold by Varian Associates, Inc., 611 Hansen Way, Palo Alto, Calif. 94303, gives excellent sensitivity and meets this requirement.

Varian presently sells an autosampler for use with its gas chromatograph. The autosampler mounts on the gas chromatograph and provides automatic, multiple sample injections to an injection port of the gas chromatograph. However, the Varian autosampler requires at least 50 microliters ($\mu$l) of sample for one injection. In certain circumstances, however, such as the aforementioned nitroglycerin assays, it may be required that the autosampler perform multiple injections with the same sample when only 50 $\mu$l or less of sample volume is available. This means that samples must be prepared again.

Therefore, it has been necessary to manually inject the samples when performing nitroglycerin assays. As a result, hours of valuable research time have been spent peforming routine sample injections. Consequently, laboratory personnel have been required to work overtime to complete analyses, resulting in physical and mental fatigue.

Hewlett-Packard sells an autosampler (HP 7673A Automatic Sampler) which can perform multiple injections with a sample volume of less than 50 $\mu$l. This is because the Hewlett-Packard autosampler does not use the entire sample during one injection. The Hewlett-Packard autosampler, however, cannot be mounted directly on the Varian VISTA 6000 gas chromatograph.

OBJECTS AND SUMMARY OF THE INVENTION

Accordingly, it is an object of the present invention to provide a gas chromatograph/autosampler coupling assembly that overcomes the aforementioned problems with the prior art.

It is another object of the present invention to provide a gas chromatograph/autosampler coupling assembly that permits automatic processing of nitroglycerin assays twenty four hours per day.

It is still another object of the present invention to provide a gas chromatograph/autosampler coupling assembly that substantially reduces the time and cost of processing nitroglycerin assays.

It is yet another object of the present invention to provide a gas chromatograph/autosampler coupling assembly that reduces operator fatigue and errors, resulting in the production of higher quality data.

It is a further object of the present invention to provide a gas chroatograph/autosampler coupling assembly that is inexpensive to manufacture and use.

In accordance with an aspect of the present invention, an assembly for coupling an autosampler mounted on a mounting plate, to a gas chromatograph having an injection site, includes bracket means for mounting the mounting plate to the gas chromatograph, the bracket means being secured to the gas chromatograph adjacent the injection site so as to permit access to the injection site by the autosampler; and securement means for securing the mounting plate on the bracket means.

In accordance with another aspect of the present invention, an assembly for coupling an autosampler to a gas chromatograph having an injection site, includes mounting plate means for holding the autosampler; bracket means for mounting the mounting plate means to the gas chromatograph, the bracket means being secured to the gas chromatograph adjacent the injection site so as to permit access to the injection site by the autosampler; and securement means for securing the mounting plate means on the bracket means.

In accordance with still another aspect of the present invention, an assembly is provided for coupling an autosampler to a gas chromatograph having an injection site, the gas chromatograph including a septum nut assembly at the injection site, the auto sampler including an injector having a base with an opening, spring means extending from the base and an injector pin extending from the base, the assembly including mounting plate means for holding the autosampler, the mounting plate means including a first opening for permitting the septum nut to mate in the opening in the base of the autosampler; a second opening; a spacer secured to the mounting plate means and extending into the second opening; an arcuate slot for receiving the injector pin when the injector is mounted on the mounting plate means; a first stabilizing plate depending from the underside of the mounting plate means; a second stabilizing plate depending from the underside of the mounting plate means;

bracket means for mounting the mounting plate means to the gas chromatograph, the bracket means being secured to the gas chromatograph adjacent the injection site so as to permit access to the injection site by the autosampler, the bracket means including a first bracket secured to the gas chromatograph on one side of the injection site, the first bracket including an inner edge facing the injection site; an angled cut-out section in alignment with the spacer and extending from the inner edge, so as to permit access of the spring means through the second hole of the mounting plate means and about the spacer to thereby removably secure the injector on the mounting plate means; a first cut-out section for receiving the first stabilizing plate to stabilize the mounting plate means and the injector on the bracket means;

a second bracket secured to the gas chromatograph on an opposite side of the injection site, the second bracket including an inner edge facing the injection site; a second cut-out section for receiving the second stabilizing plate to stabilize the mounting plate means and the injector on the bracket means; and securement means for securing the mounting plate means on the bracket means, the securement means including a first hole in the first bracket; a second hole in the second bracket; a third hole in the mounting plate means in alignment with the first hole when the mounting plate means is positioned on the bracket means; a fourth hole in the mounting plate means in alignment with the third hole when the mounting plate means is positioned on the bracket means; a first securing screw extending through the first and third holes; and a second securing screw extending through the second and third holes, wherein the first and second securing screws secure the mounting plate means on the bracket means with a two-point securement.

The above and other objects, features and advantages of the present invention will become readily apparent from the following detailed description which is to be read in connection with the accompanying drawings.

DETAILED DESCRIPTION OF A PREFERRED EMBODIMENT

Figure 1:
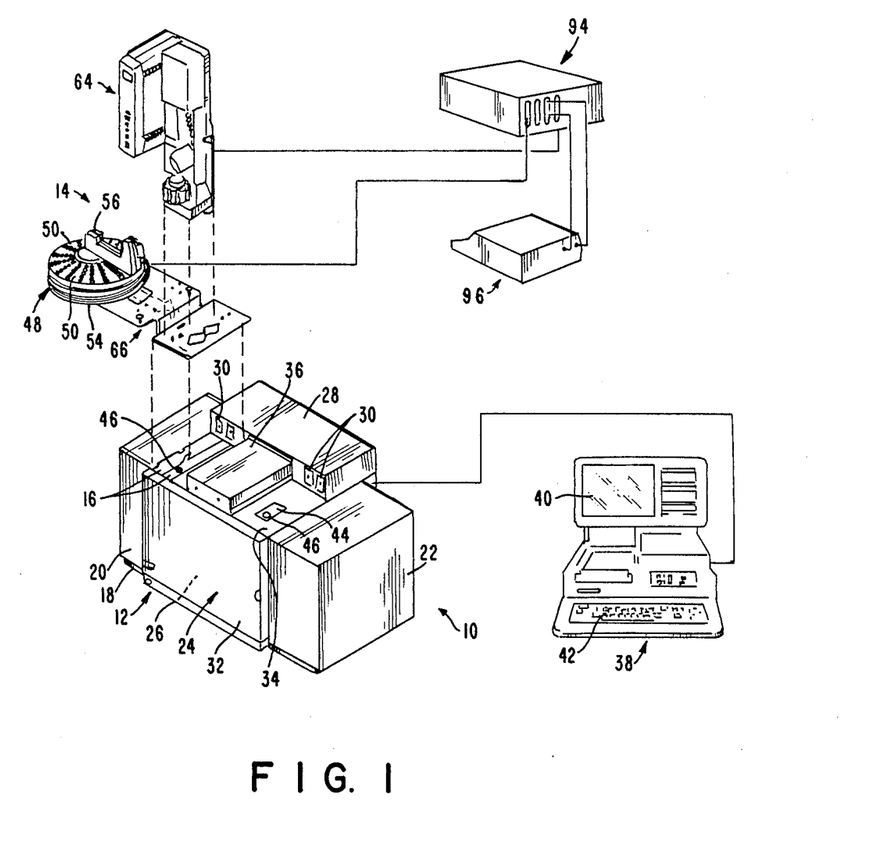
FIG. 1 is a perspective view of apparatus for performing automatic gas chromatograph assays according to the present invention.

Referring to the drawings in detail, and initially to FIG. 1 thereof, apparaus 10 for performing automatic gas chromatograph assays generally includes a gas chromatograph 12, an autosampler 14 and a coupling assembly 16 for coupling the gas chromatograph 12 to autosampler 14.

More specifically, in a preferred embodiment of the present invention, gas chromaytograph 12 is a VISTA 6000 gas chromatograph sold by Varian Associates, Inc., 611 Hansen Way, Palo Alto, Calif. 94303. The Varian gas chromatograph uses two microprocessors (not shown) to provide a dual channel instrument and is composed of three basic modules mounted on a common base 18. Specifically, there is a lower electronics module 20, a pneumatics module 22 and a main frame module 24, the latter including a multi-ramp programmable column oven 26 and an upper electronics cabinet 28. Lower electronics module 20 and upper electronics cabinet 28 include various printed circuit boards (not shown) for controlling the operation of gas chromatograph 12, with upper electronics cabinet 28 being provided with various control knobs and switches 30. Pneumatics module 22 contains the filters, digital flow controllers, pressure regulators, air/H$_2$ valves, make-up valves, pressure gauges, cryogenic valves and column-switching actuators. Column oven 26 is located behind a column oven door 32 and underneath instrument top covers 34.

Further, gas chromatograph 12 includes a detector cabinet 36 installed above column oven 26 of main frame module 24, and which includes, for example, a thermal conductivity detector, an electron capture detector and the like. The detectors of detector cabinet 36 profect through the top of and into column oven 26.

Gas chromatograph 12 can be controlled by a computer system 38, such as the VISTA 402 data system sold by Varian, which includes a cathode ray tube (CRT) 40 and keyboard 42. Computer system 38 executes automation and external event applications, and can process, store, and print peak data and reports.

For purposes of the present invention, a detailed description of the above components of the Varian gas chromatograph 12 is unnecessary.

Varian gas chromatograph 12 further includes injectors and injector ovens (not shown) located beneath instrument top covers 34. In the VISTA 6000 model gas chromatograph, one injector is located on each side of the apparatus, each equidistant from detector cabinet 36. An injector cover 44 is positioned on each instrument top cover 34, in covering relation to the respective injector, with each injector cover including an injection site or port 46. In this manner, a needle (not shown) containing a sample can be injected through each site 46 into the respective injector in order to perform a gas chromatographic analysis with respect to the same.

As described above, Varian does sell an auto sampler for use with Varian gas chromatograph 12. The autosampler mounts on Varian gas chromatograph 12 and provides automatic, multiple sample injections to an injection port 46. Thus, if automatic injection is required, a predrilled and fitted instrument top cover (not shown) is provided for gas chromatograph 12 to permit proper mounting of the autosampler. However, as also described above, such autosampler is unsuitable for use with Varian gas chromatograph 12 when using the latter for nitroglycerin assays.

As described above, the Varian autosampler requires at least 50 microliters (μl) of sample for one injection. However, when performing nitroglycerin assays, it may be required that the autosampler perform multiple injections with the same sample when only 50 μl or less of sample volume is available. This means that, with the Varian autosampler, samples must be prepared again. Therefore, it has been necessary to manually inject the samples when performing nitroglycerin assays. As a result, hours of valuable research time have been spent performing routine sample injections. Consequently, laboratory personnel have been required to work overtime to complete analyses, resulting in physical and mental fatigue.

Hewlett-Packard sells and autosampler (HP 7673A Automatic Sampler) which can perform multiple injections with a sample volume of less than 50 μl. This is because the Hewlett-Packard autosampler does not use the entire sample during one injection.

Figure 2:
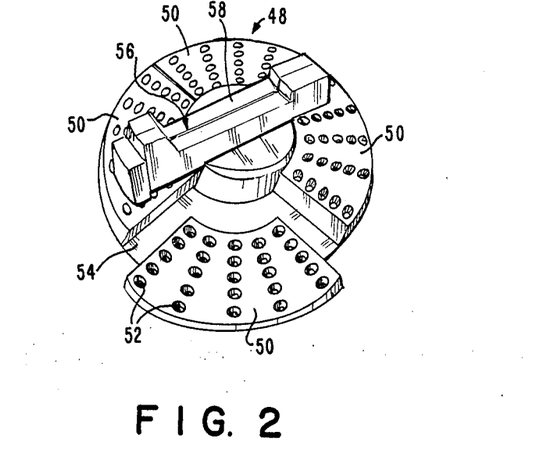
FIG. 2 is a perspective view of the quadrant trays of the autosampler of FIG. 1.
Figure 3:
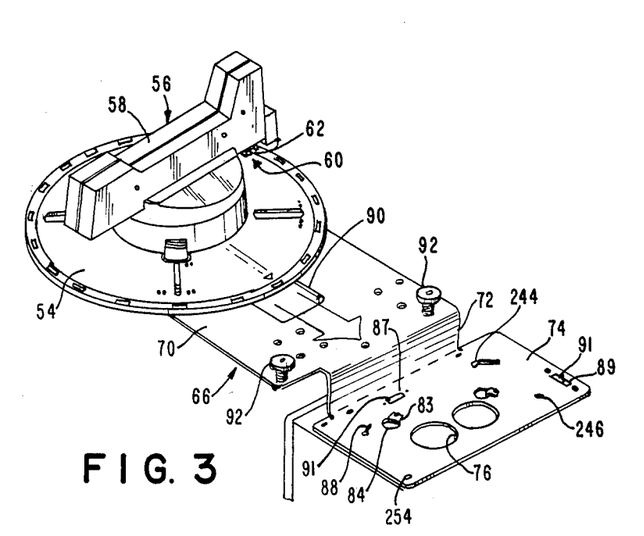
FIG. 3 is a perspective view of the tray base and mounting plate of the autosampler of FIG. 1.

Specifically, as shown in FIGS. 1 and 2, the Hewlett-Packard autosampler 14 includes a circular tray 48 which functions as the storage and transportation vehicle for up to 100 sample vials. Tray 48 is formed by four removable quadrant trays 50, each quadrant tray 50 containing five rows of five recesses 52, each recess 5i adapted to contain a sample vial, and with all four trays 50 mounted on a circular tray base 54 (FIGS. 2 and 3). Quadrant trays 50 are formed as hollow plastic molded parts so as to provide passages (not shown) for circulation of fluid for moderate temperature control of the sample vials.

A transport mechanism 56 is positioned on tray base 54 at the center of quadrant trays 50, and includes an arm 58 and a gripper 60 at the end of arm 58 for gripping the vials stored on trays 50. Transport mechanism 56 is capable of movement in three directions, that is, radially, about its axis and vertically. Specifically, arm 58 can move in the radial and axial direction, while gripper 60 can move in the vertical direction. When picking up a vial, arm 58 positions gripper 60 beside the vial, then rotates to snap to claw 62 of gripper 60 onto the neck of the vial. The individual sample vials are moved from tray 48 to the injector 64 of Hewlett-Packard autosampler 14, and back, by the transport mechanism 56.

Figure 4:
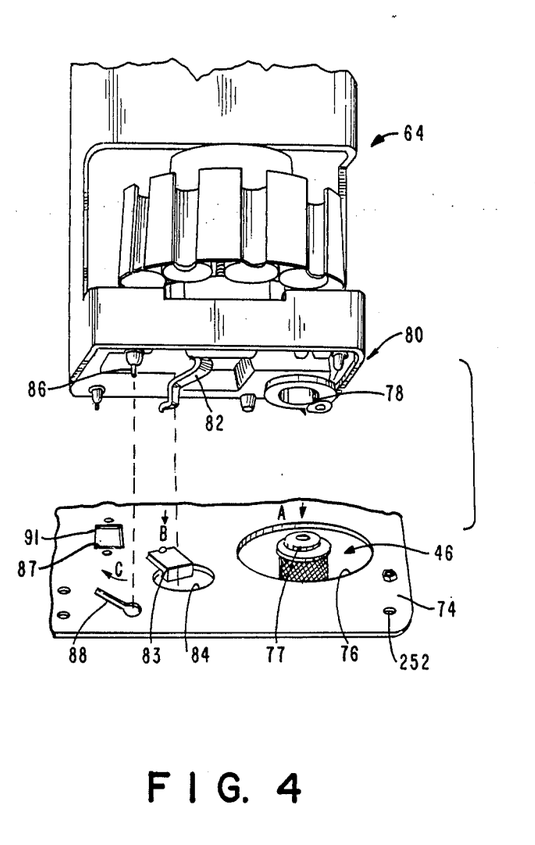
FIG. 4 is a perspective view showing the assembly of the injector of the autosampler of FIG. 1 onto the mounting plate.
Figures 5, 6:
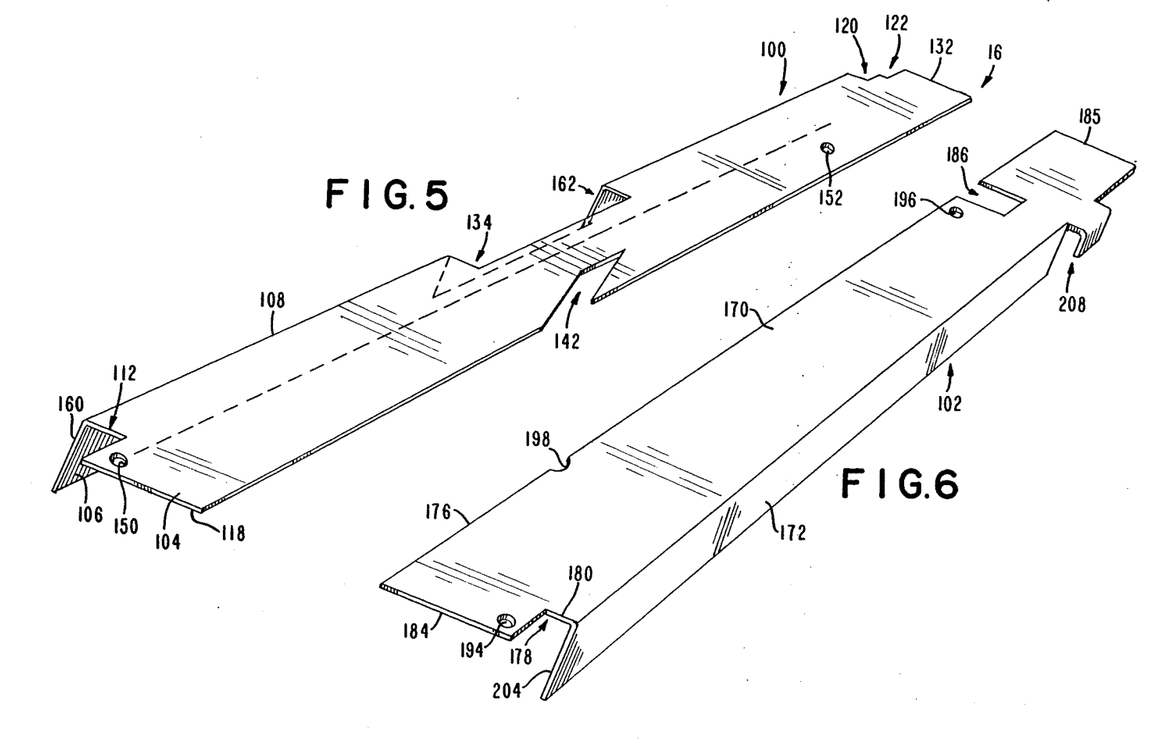
FIG. 5 is a perspective view of one bracket of the coupling assembly of FIG. 1.
FIG. 6 is a perspective view of the other bracket of the coupling assembly of FIG. 1.

Injector 64 normally mounts to a mounting plate 66 directly over the injection port 46 of a Hewlett-Packard gas chromatograph, as shown in FIG. 4. Mounting plate 66 is formed in a substantially Z-configuration with a horizontal securing plate section 70 to which circular tray base 54 is mounted and secured, a short vertical plate section 72 extending downwardly from one free end of securing plate section 70, and a horizontal mounting plate section 74 extending from the opposite free end of vertical plate section 72, with mounting plate section 74 being positioned and secured over the injection site or port 46.

As shown in FIG. 4, a septum nut 77 at the injection site or port 46 extends through an opening 76 in mounting plate section 74 and through an opening 78 in the base 80 of injector 64, as indicated by arrow A, to provide precise alignment. A syringe needle (not shown) is provided in opening 78 for supplying the sample to injection site 46. In addition, a bayonet spring clip 82 on the bottom of injector 64 engages a locating hole 84 in mounting plate section 74, as indicated by arrow B. As will be appreciated, bayonet spring clip 82 extends through locating hole 84 and engages the underside of mounting plate section 74. In order to increase the spring action of bayonet spring clip 82, a spacer 83 is secured to mounting plate section 74 and extends into locating hole 84 to effectively increase the width of mounting plate section 74 thereat, and thereby, increase the extent to which bayonet spring clip 82 is biased at the underside of mounting plate section 74. Further, an alignment pin 86 on the bottom of injector 64 engages a locating slot 88 in mounting plate section 74. When the above assembly has been completed, and with the base 80 of injector 64 resting flat on mounting plate section 74, which is normally located on the Hewlett-Packard gas chromatograph, injector 64 is turned one-eight turn clockwise until injector 64 is locked in place.

In addition, two rectangular openings 87 and 89 are provided in horizontal mounting plate section 74, and a T-shaped stabilizing plate 91 is secured in each opening 87 and 89.

Further, tray base 54 has a center post (not shown) at its underside, which fits within a slot 90 in securing section 70 until the peripheral edge of tray base 54 fits beneath circular stops 92 thereon, as shown in FIG. 3. As shown best in FIGS. 15 and 16, slot 90 effectively creates two parallel, bifurcated arms 97 and 99 of securing section 70.

In order to control the operation of the Hewlett-Packard autosampler 14, a Hewlett-Packard autosampler controller 94 is connected with transport mechanism 56 and injector 64, and a Hewlett-Packard 3393A integrator 96 is connected with controller 94. Thus, integrator 96, through controller 94, provides a sequence which is a set of parameters which guides autosampler 14 through a series of injections to gas chromatograph 12. A sequence always references a method file or uses the active method parameters to define the operation of the autosampler. Together, a method and a sequence determine how a series of analyses are to be carried out.

Thus, with the Hewlett-Packard autosampler 14, 1 to 100 samples may be automatically injected into the gas chromatograph.

However, as discussed above, there is no provision for mounting Hewlett-Packard autosampler 14 directly on the Varian VISTA 6000 gas chromatograph 12.

The present invention overcomes this problem by providing coupling assembly 16 for connecting a Hewlett-Packard autosampler 14 directly on a Varian VISTA 6000 gas chromatograph 12 in order to provide a gas chromatograph with the necesary sensitivity coupled with an autosampler that can perform multiple injections on the same sample when only 50 μl of sample volume is available.

Specifically, coupling assembly 16 is formed by two brackets 100 and 102, as shown in FIGS. 5–12. Bracket 100 is formed as a substantially L-shaped bracket having a horizontal leg plate 104 and a vertical leg plate 106 extending downwardly from one lengthwise edge 108 of horizontal leg plate 104.

Figure 8:
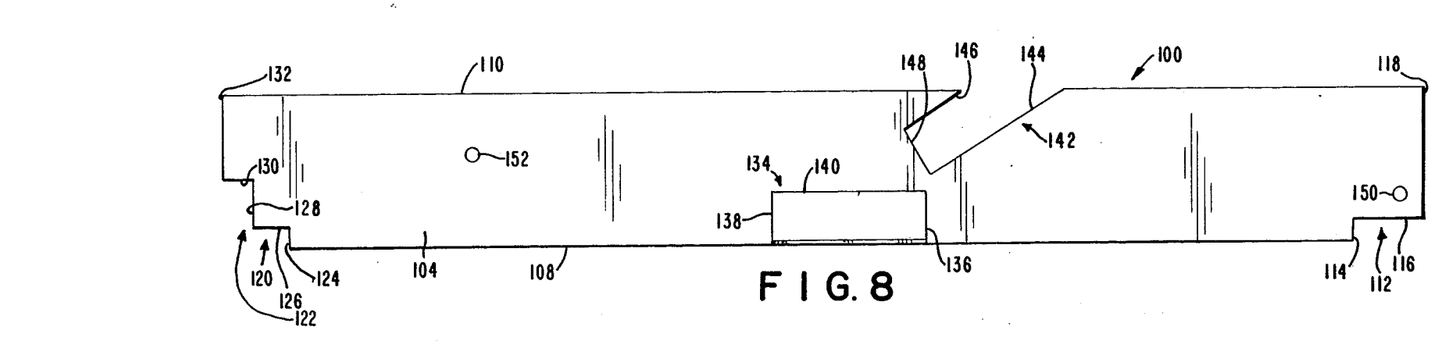
FIG. 8 is a top plan view of the bracket of FIG. 5.
Figure 9:
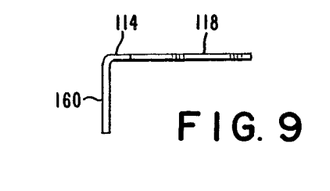
FIG. 9 is an end elevational view of the bracket of FIG. 5.

As shown best in FIG. 8, horizontal leg plate 104 includes opposite and parallel lengthwise edges 108 and 110 having lengths of 27.0 centimeters (cm) and 30.5 cm, respectively. At one end of lengthwise edge 108, a single inwardly directed step 112 is formed having a widthwise step edge 114 of 0.4 cm and a lengthwise step edge 116 of 1.8 cm. Widthwise step edge 114 is perpendicular to lengthwise edge 108 and lengthwise step edge 116 is parallel to lengthwise edge 108. A transverse edge 118 of horizontal leg plate 104, having a dimension of 3.4 cm, connects the end of lengthwise step edge 116 to one end of lengthwise edge 110 and is perpendicular thereto.

At the opposite end of lengthwise edge 108, two inwardly directed steps 120 and 122 are formed. Specifically, step 120 is formed having a widthwise step edge 124 of 0.5 cm and a lengthwise step edge 126 of 0.9 cm, followed by step 122 having a widthwise step edge 128 of 1.2 cm and a lengthwise step edge 130 of 0.8 cm. Widthwise step edges 124 and 128 are perpendicular to lengthwise edge 108 and lengthwise step edges 126 and 130 are parallel to lengthwise edge 108. A transverse edge 132 of horizontal leg plate 104, having a dimension of 2.2 cm, connects the end of lengthwise step edge 130 to the opposite end of lengthwise edge 110 and is perpendicular thereto.

Further, horizontal leg plate 104 includes a rectangular cut-out section 134 having widthwise cut-out edges 136 and 138 of 1.4 cm and a lengthwise cut-out edge 140 of 4.0 cm. The last lengthwise cut-out edge is formed in line with lengthwise edge 108. Cut-out edge 136 is formed a distance of 10.8 cm from widthwise step edge 114, and cut-out edge 138 is formed a distance of 12.2 cm from widthwise step edge 124.

An angled cut-out section 142 is formed at the opposite edge 110 of horizontal leg plate 104. Specifically, angled cut-out section 142 includes a first angled cut-out edge 144 extending inwardly from lengthwise edge 110 for a distance of 4.0 cm, starting at a distance of 9.2 cm from transverse edge 118, and angled at approximately 33 degrees with respect to lengthwise edge 110 away from transverse edge 118. Angled cut-out section 142 further includes a second angled cut-out edge 146 extending inwardly from lengthwise edge 110 for a distance of 1.9 cm, starting at a distance of 18.8 cm from transverse edge 132, and angled at approximately 33 degrees with respect to lengthwise edge 110 away from transverse edge 118. Thus, angled cut-out edges 144 and 146 are parallel to each other and spaced from each other by a distance of 2.5 cm. The inward ends of angled cut-out edges 144 and 146 are connected together by a cut-out edge 148 of 1.4 cm and which is perpendicular to angled cut-out edges 144 and 146.

Finally, horizontal leg plate 104 includes two circular holes 150 and 152. Hole 150 is a 3/16 inch diameter hole formed with its center 2.75 cm from lengthwise edge 110 and 0.6 cm from transverse edge 118, and is provided to secure bracket 100 to an existing hole in the Varian VISTA 6000 gas chromatograph 12, with a screw. Hole 152 is sized to receive a ⅛ inch self tapping screw and is formed with its center 1.6 cm from lengthwise edge 110 and 6.3 cm from transverse edge 132. Hole 152 is provided to secured the Hewlett-Packard autosampler 14 thereto.

Figure 7:
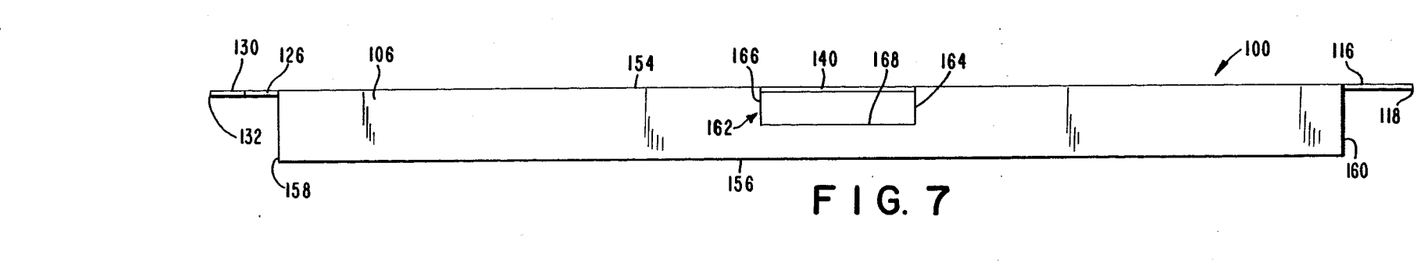
FIG. 7 is a side elevational view of the bracket of FIG. 5.

As best shown in FIG. 7, vertical leg plate 106 is formed as a rectangular plate with upper and lower lengthwise edges 154 and 156 of 27.0 cm and widthwise edges 158 and 160 of 1.9 cm, with widthwise edge 158 being in-line with widthwise step edge 124 and forming a continuation thereof, with widthwise edge 160 being in-line with widthwise step edge 114 and forming a continuation thereof, and with upper lengthwise edge 154 being identical, that is colinear with, lengthwise edge 108 of horizontal leg plate 104.

In addition, vertical leg plate 106 is formed with a rectangular cut-out section 162 formed as a continuation of rectangular cut-out section 134. Specifically, rectangular cut-out section 162 is formed with widthwise cut-out edges 164 and 166 of 1 cm, which are continuations of and in-line with widthwise cut-out edges 136 and 138, respectively. Widthwise cut-out edge 164 starts at upper lengthwise edge 154 a distance of 10.8 cm from widthwise edge 160 and is perpendicular to upper lengthwise edge 154. Widthwise cut-out edge 166 starts at upper lengthwise edge 154 a distance of 12.2 cm from widthwise edge 158 and is perpendicular to upper lengthwise edge 154. The lower ends of widthwise cut-out edges 164 and 166 are connected by a lower lengthwise cut-out edge 168 which is parallel to lengthwise edge 154 and has a dimension of 4.0 cm.

Figure 10:
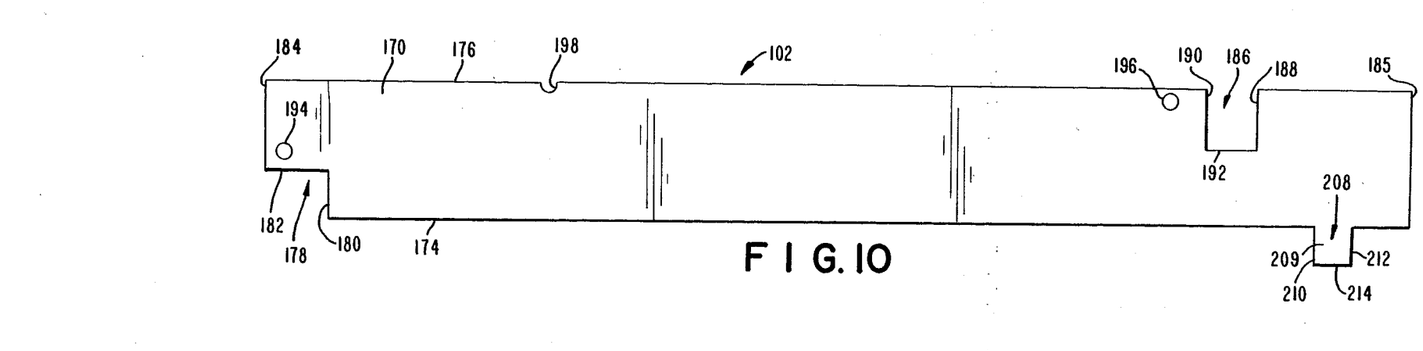
FIG. 10 is a top plan view of the bracket of FIG. 6.

Bracket 102 is also formed as a substantially L-shaped bracket having a horizontal leg plate 170 and a vertical leg plate 172 extending downwardly from one lengthwise edge 174 of horizontal leg plate 170.

As shown best in FIG. 10, horizontal leg plate 170 includes opposite and parallel lengthwise edges 174 and 176 having lengths of 28.7 cm and 30.5 cm, respectively. At one end of lengthwise edge 174, a single inwardly directed step 178 is formed having a widthwise step edge 180 of 1.2 cm and a lengthwise step edge 182 of 1.8 cm. Widthwise step edge 180 is perpendicular to lengthwise edge 174 and lengthwise step edge 182 is parallel to lengthwise edge 174. A transverse edge 184 of horizontal leg plate 170, having a dimension of 2.5 cm, connects the end of lengthwise step edge 182 to one end of lengthwise edge 176 and is perpendicular thereto. A transverse edge 185 connects the opposite ends of lengthwise edges 174 and 176 and has a dimension of 3.7 cm. Transverse edges 184 and 185 are perpendicular to lengthwise edges 174 and 176.

Further, horizontal leg plate 170 includes a rectangular cut-out section 186 having widthwise cut-out edges 188 and 190 of 1.7 cm and a lengthwise cut-out edge 192 of 1.3 cm. The last lengthwise cut-out edge is formed in line with lengthwise edge 176. Cut-out edge 188 is formed a distance of 4.0 cm from transverse edge 185, and cut-out edge 190 is formed a distance of 25.2 cm from transverse edge 184.

Horizontal leg plate 170 also includes two circular holes 194 and 196. Hole 194 is a 3/16 inch diameter hole formed with its center 1.9 cm from lengthwise edge 176 and 0.6 cm from transverse edge 184, and is provided to secure bracket 102 to an existing hole in the Varian VISTA 6000 gas chromatograph 12, with a screw or bolt. Hole 196 is sized to receive a 1/8 inch self tapping screw and is formed with its center 3.4 cm from lengthwise edge 174 and 0.9 cm from widthwise cut-out edge 190. Hole 196 is provided to secure the Hewlett-Packard autosampler 14 thereto.

Finally, horizontal leg plate 170 is formed with a sime-circular slot 198 having a radial dimension of 0.2 cm, at lengthwise edge 176. The center of slot 198 is spaced 7.6 cm from transverse edge 184. Slot 198, along with a both, nut and washer, is provided to secure the Hewlett-Packard autosampler 14 thereto.

Figure 11:
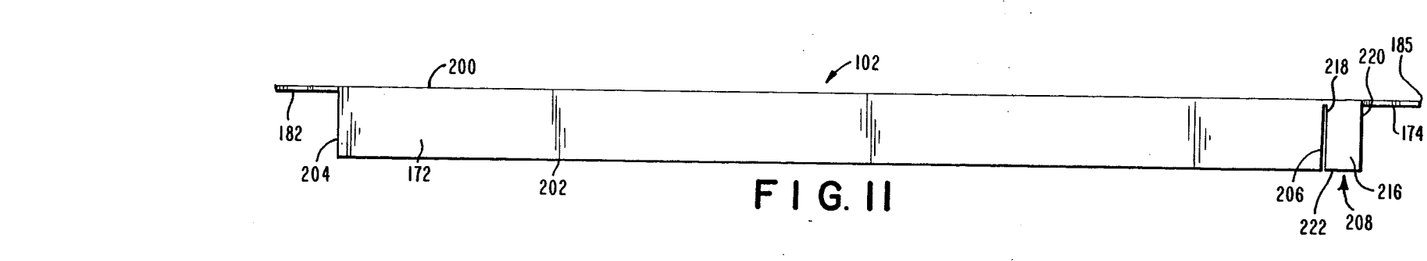
FIG. 11 is a side elevational view of the bracket of FIG. 6.
Figure 12:
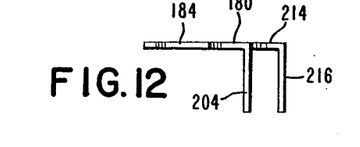
FIG. 12 is an end elevational view of the bracket of FIG. 6.

As best shown in FIG. 11, vertical leg plate 172 is formed as a rectangular plate with upper and lower lengthwise edges 200 and 202 of 26.3 cm and widthwise edges 204 and 206 of 1.9 cm, with widthwise edge 204 being in-line with widthwise step edge 180 and forming a continuation thereof, and with upper lengthwise edge 200 being identical, that is, collinear with, lengthwise edge 174 of horizontal leg plate 170.

In addition, bracket 102 is formed with an L-shaped tab 208 immediately adjacent widthwise edge 206 of vertical leg plate 172. Tab 208 thereby includes a horizontal tab section 209 of a rectangular configuration, with opposite widthwise tab edges 210 and 212 of 1.0 cm, a lengthwise tab edge 214 of 1.0 cm which connects the ends to tab edges 210 and 212, and another lengthwise tab edge which forms part of lenthwise edge 174 of horizontal leg plate 170. Widthwise tab edge 212 is spaced 1.4 cm from transverse edge 185. Tab 208 further includess a downwardly extending vertical tab section 216 of a rectangular configuration connected at tab edge 214, with opposite widthwise tab edges 218 and 220 of 1.9 cm, a lenthwise tab edge 222 of 1.0 cm which connects the ends of tab edges 218 and 220, and another lengthwise tab edge which is identical to lengthwise tab edge 214.

Figure 13:
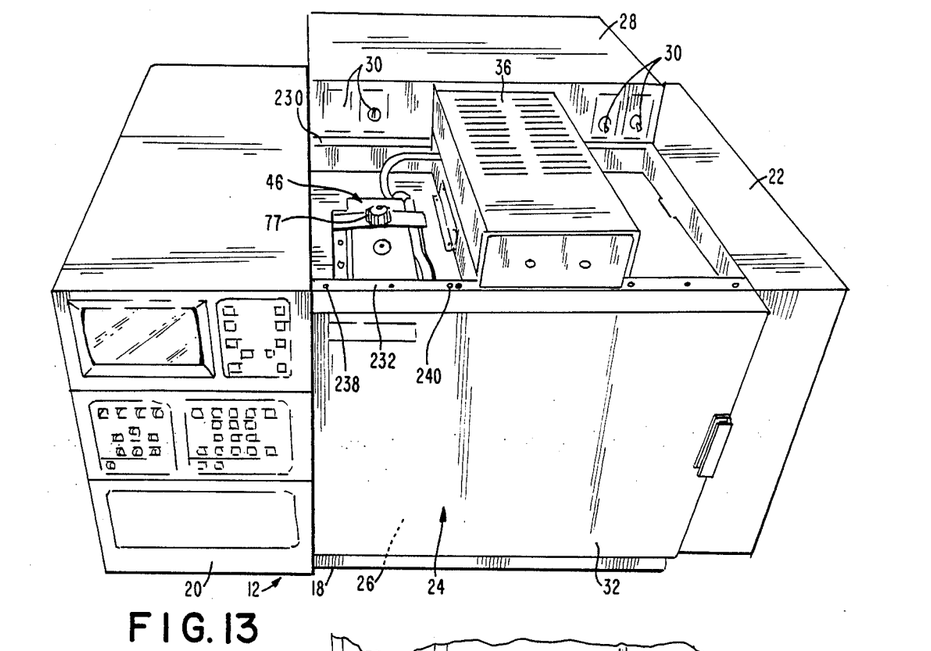
FIG. 13 is a perspective view of the gas chromatograph of FIG. 1.

A description will now be given with respect to FIGS. 13-18 as to the assembly of Hewlett-Packard autosampler 14 with a Varian VISTA 6000 gas chromatograph 12. Specifically, a Varian gas chromatograph 12 is shown in FIG. 13 with its instrument top covers disassembled therefrom so as to completely expose injection port 46 and septum nut 77. As shown best in FIG. 14, two transverse support shelves 230 and 232 are secured at the front and rear portions of Varian gas chromatograph 12, on opposite sides of each injection port 46. Bracket 100 according to the present invention is secured on top of shelves 230 and 232, extending transversely across such shelves 230 and 232 and to one side thereof. In like manner, bracket 102 according to the present invention is secured on top of shelves 230 and 232, extending transversely across such shelves 230 and 232 and to the opposite side thereof, with bracket 102 being spaced from and arranged parallel to bracket 100. It will be appreciated that, with this arrangement, brackets 100 and 102 and shelves 230 and 232 are arranged effectively in a rectangular configuration, with septum nut 77 positioned substantially centrally therein. In order to secure brackets 100 and 102 in such position, bolts or screws 234 and 236 extend through holes 150 and 194 in brackets 100 and 102, respectively, and are threadedly received in threaded holes 238 and 240 in shelf 232.

Figure 14:
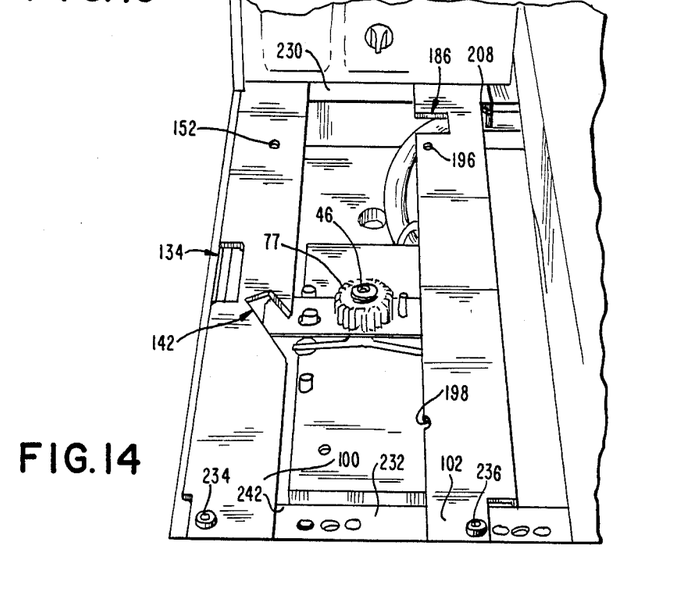
FIG. 14 is an enlarged perspective view of a portion of the gas chromatograph of FIG. 13, with the brackets of FIGS. 5 and 6 secured thereon.

Further, with this arrangement, brackets 100 and 102 are arranged such that angled cut-out section 142 of bracket 100 is on the inner side of bracket 100 facing bracket 102 and cut-out section 134 is on the opposite outer side thereof, and cut-out section 186 of bracket 102 is on the inner side of bracket 102 facing bracket 100. In addition, lengthwise step edge 182 of bracket 102 is dimensioned so that widthwise step edge 180 is immediately adjacent the lengthwise inner edge 242 of shelf 232. Still further, with such arrangement, tab 208 extendss down adjacent one end (not shown) of shelf 230.

Figure 15:
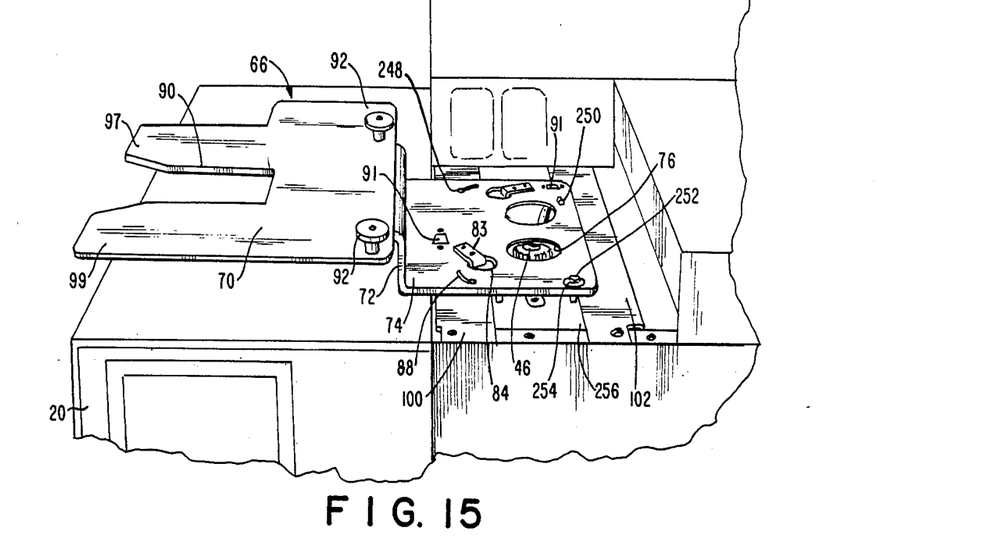
FIG. 15 is an enlarged perspective view of the portion of the gas chromatograph of FIG. 14, with the mounting plate mounted on the brackets.

Thereafter, as shown in FIG. 15, mounting plate 66 is secured thereover. Specifically, horizontal mounting plate section 74 is positioned over brackets 100 and 102, with horizontal securing plate section 70 being positioned above the upper surface of lower electronics module 20. In this regard, slot 244 and hole 246 (FIG. 3) in horizontal mounting plate section 74 are aligned with holes 152 and 196 of brackets 100 and 102, respectively. Accordingly, bolts or screws 248 and 250 extend through slot 244 and holes 246, and are threadedly received in holes 152 and 196 to secure horizontal mounting plate section 74 in position. It will be appreciated from FIG. 15, that in this position, the leftmost portion of horizontal mounting plate section 74 rests on the upper surface of lower electronics module 20 for support. At the same time, a bolt 252 is received in a hole 254 (FIG. 3) of horizontal mounting plate section 74. In this manner, bolt 252 fits within slot 198 in bracket 102 and provides stability to horizontal mounting plate section 74.

It will further be appreciated that spacer 83 is in alignment with, and fits within, angled cut-out section 142 of bracket 100. Also, T-shaped stabilizing plate 91 in rectangular opening 87 of mounting plate section 74 fits snugly withing rectangular cut-out section 134, while T-shaped stabilizing plate 91 in rectangular opening 89 fits snugly within rectangular cut-out section 186, thereby further stabilizing horizontal mounting plate section 74.

Figure 16:
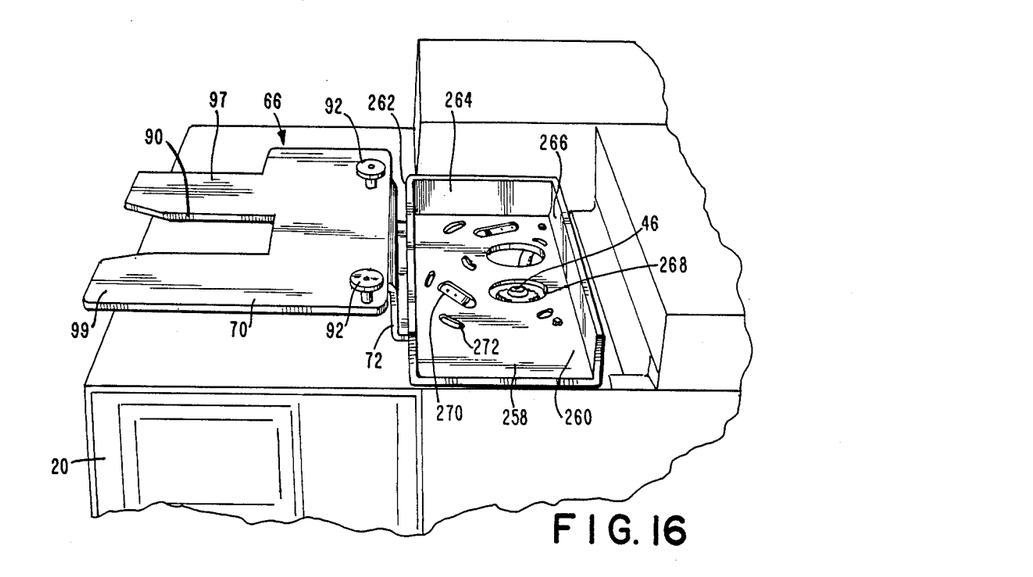
FIG. 16 is an enlarged perspective view of the portion of the gas chromatograph of FIG. 15, with a tray mounted on the mounting plate.

A plastic rectangular tray 258 having a bottom 260, and three side walls 262, 264 and 266, is mounted on top of horizontal mounting plate section 74, as shown in FIG. 16, with the front of tray 258 being open. Tray 258 includes a hole 268 in alignment with opening 76 of horizontal mounting plate section 74, an elongated slot 270 in alignment with hole 84 and spacer 83, and an elongated slot 272 in alignment with slot 88. In this manner, septum nut 77 and opening 78 in base 80 mate through opening 76 in horizontal mounting plate section 74 and hole 268 in tray 258. In addition, bayonet spring clip 82 extends through slot 270 and hole 84, and alignment pin 86 extends through slots 272 and 88, wherein base 80 of injector 64 rests on the upper surface of tray 258. It will be appreciated that a major purpose of tray 258 is to effectively increase the width of horizontal mounting plate section 74 to further bias bayonet spring clip 82, and thereby increase the spring force thereby in the assembled condition so as to enhance the stability of injector 64 on tray 258.

Figure 17:
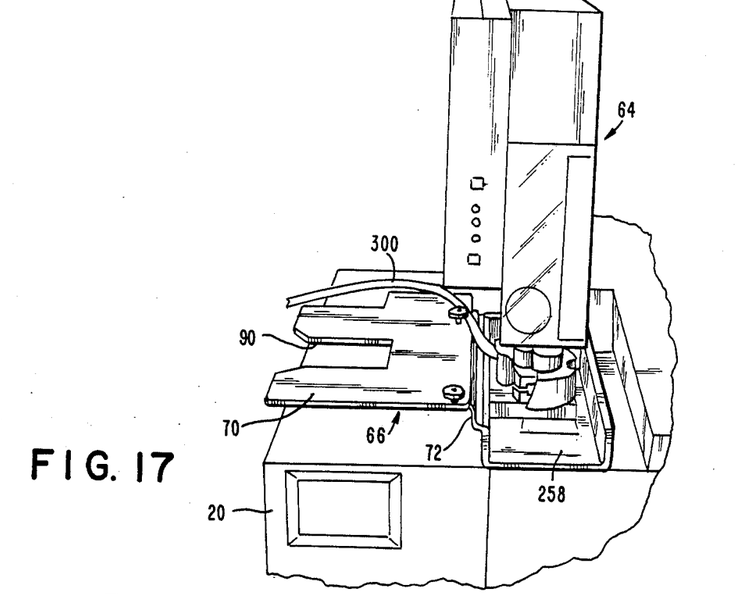
FIG. 17 is an enlarged perspective view of the portion of the gas chromatograph on FIG. 16, with the injector mounted on the tray and the mounting plate.
Figure 18:
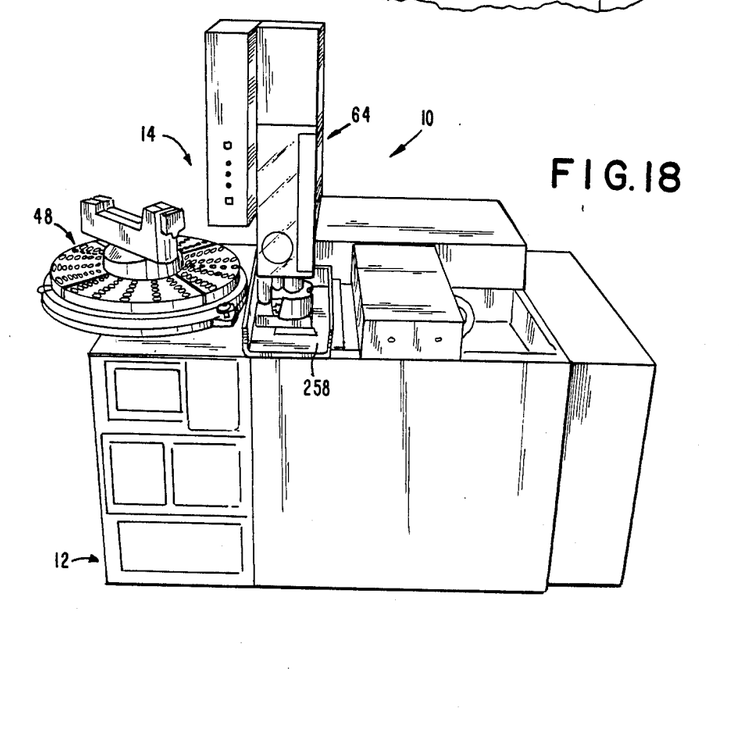
FIG. 18 is an enlarged perspective view of the gas chromatograph of FIG. 13, with the autosampler mounted thereon.

As shown in FIG. 17, injector 64 is then assembled in place on top of tray 258 in the manner previously described with respect to FIG. 4. Then, circular tray 48 is positioned on horizontal securing plate section 70 such that a lower center post (not shown) thereof extends in slot 90 and with the peripheral edge of tray base 54 positioned under, and held down by, stops 92. Thereafter, all of the appropriate electrical connections are made with conduit 300 shown in FIG. 17.

Thus, with apparatus 10 described above, in which a Varian VISTA 6000 gas chromatograph 12 and a Hewlett-Packard autosampler 14 are combined by coupling assembly 16, apparatus 10 operates as an integrated gas chromatography system. The sequence of operation begins by entering operating parameters on the Varian VISTA 6000 gas chromatograph. Gas chromatograph 12 stabilizes to the setpoint conditions, such as oven temperature, detector temperature, and the like, and thereafter advances to the ready state. Data collection parameters, such as the sample identification numbers, are then entered on the Varian VISTA 402 data system 38, which is then prepared for data collection. Finally, the Hewlett-Packard autosampler 14 is readied for an injection sequence by entering operating parameters, such as the sample volume, the number of vials, the stop time, and the like, through the Hewltt-Packard 3393A integrator 96.

When all systems are ready, autosampler 14 is started and a sample is injected. As the injection is made, the syringe barrel depresses a start switch located directly above the injector nut, and the gas chromatograph run sequence and data collection operations begin. To ensure contact of the syringe barrel with the start switch, a septum with a hole is adhered to the start switch. The septum also provides a cushioned interface between the syringe barrel and start switch. The autosampler 14 is operated in the on-column injection mode, rather than in the split/splitless mode. This is because, when operated in the injection mode, the syringe barrel lowers itself 19 mm lower than in the split/splitless mode. When the analysis is complete, gas chromatograph 12 and data system 38 ready themselves for the next injection, and so on.

With the above combination of a Varian VISTA 6000 gas chromatograph 12 and a Hewlett-Packard autosampler 14, processing of nitroglycerin assays can be performed 24 hours per day. This results in a significant savings of time and money. Further, there is less operator fatigue, fewer errors, and thereby, higher quality data, particularly when performing nitroglycerin analyses.

It will be appreciated that although the above discussion has been provided with respect to the coupling of a Varian VISTA 6000 gas chromatograph with a Hewlett-Packard autosampler, the present invention has wider applicability, and it may be used to couple other gas chromatographs and autosamplers which have prior to the present invention been incompatible.

It will further be appreciated that, while two separate brackets 100 and 102 have been provided, the number of components can be varied. For example, brackets 100 and 102 can be incorporated into a single bracket provided with a central opening that approximates the spacing between 100 and 102 in assembled condition.

As another alternative, although two brackets 100 and 102 have been shown, bracket 100 can be eliminated. In such case, bolt 248 would extend through another hole (not shown) in bracket 102 so as to provide a two-point securement of horizontal mounting plate section 74 thereon, that is by bolts or screws 248 and 250 both extending through bracket 102. In such case, horizontal mounting plate section 74 would extend across bracket 102 and the upper surface of lower electronics module 20.

Having described a specific preferred embodiment of the invention with reference to the accompanying drawings, it will be appreciated that the present invention is not limited to that precise embodiment, and that various changes and modifications may be effected therein by one of ordinary skill in the art without departing from the scope or spirit of the invention as defined in the appended claims.

What is claimed is:

1. An assembly for coupling an autosampler mounted on a mounting plate, to a gas chromatograph having an injection site, said assembly comprising:
bracket means for mounting said mounting plate to said gas chromatograph, said bracket means being secured to said gas chromatograph adjacent injection site so as to permit access to said injection site by said autosampler; and
securement means for securing said mounting plate on said bracket means.

2. An assembly according to claim 1; wherein said securement means includes two holes in said bracket means, two holes in said mounting plate which are in alignment with said two holes of said bracket means, and screw means extending through said two holes of said mounting plate and said two holes of said bracket means for securing said mounting plate on said bracket means with a two-point securement.

3. An assembly accoring to claim 2; wherein said bracket means includes a first bracket and a second bracket secured to said gas chromatograph on opposite sides of said injection site, said first bracket including a first one of said holes and said second bracket including a second one of said holes.

4. An assembly according to claim 1; wherein said gas chromatograph includes a septum nut assemby at said injection site, said autosampler includes an injector having a base with an opening, and said mounting plate includes an opening, with said septum nut mating in said opening in said base of siad autosampler through said opening in said mounting plate.

5. An assembly according to claim 1; wherein said mounting plate includes an opening and a spacer secured to said mounting plate and extending into said opening, said autosampler includes an injector having a base with spring means for engaging with said spacer through said opening in said mounting plate to removably secure said injector on said mounting plate, and said bracket means includes an angled cut-out section is alignment with said spacer to permit access of said spring means under said spacer.

6. An assembly according to claim 5; wherein said bracket means includes a first bracket and a second bracket secured to said gas chromatograph on opposite sides of said injection site, said first bracket including an inner edge facing said injection site and said angled cut-out section extending in said first bracket from said inner edge.

7. An assembly according to claim 1; wherein said mounting plate includes an arcuate slot, and said autosampler includes an injector having an alignment pin extending into said arcuate slot when said injector is mounted on said mounting plate.

8. An assembly according to claim 1; wherein said mounting plate includes a first stabilizing plate secured thereto and depending from the underside thereof, and said bracket means includes a first cut-out section for receiving said first stabilizing plate to stabilize said mounting plate and said injector on said bracket means.

9. An assembly according to claim 8; wherein said mounting plate includes a second stabilizing plate secured thereto and depending from the underside thereof, and said bracket means includes a second cut-out section for receiving said second stabilizing plate to stabilize said mounting plate and said injector on said bracket means.

10. An assembly according to claim 9; wherein said bracket means includes a first bracket and a second bracket secured to said gas chromatograph on opposite sides of said injection site, said first bracket including said first cut-out section and said second bracket including said second cut-out section.

11. An assembly according to claim 1; wherein said bracket means includes a first bracket and a second bracket secured to said gas chromatograph on opposite sides of said injection site.

12. An assembly according to claim 11; wherein said first bracket includes:
an inner edge facing said injection site; an opposite outer edge; an angled cut-out section extending from said inner edge;
a first cut-out section extending from said outer edge;
a first hole for receiving screw means for securing said first bracket to said gas chromatograph; and a second hole for receiving screw means for securing said mounting plate on said first bracket; and
said second bracket includes:
an inner edge facing said injection site;
an opposite outer edge;
a second cut-out section extending from said inner edge of said second bracket;
a third hole for receiving screw means for securing said second bracket to said gas chromatograph; and
a fourth hole for receiving screw means for securing said mounting plate on said second bracket.

13. An assembly for coupling a autosampler to a gas chromatograph having an injection site, said assembly comprising:
mounting plate means for holding said autosampler;
bracket means for mounting said mounting plate means to said gas chromatograph, said bracket means being secured to said gas chromatograph adjacent said injection site so as to permit access to said injection site by said autosampler; and
securement means for securing said mounting plate means on said bracket means.

14. An assembly according to claim 13; wherein said securement means includes two holes in said bracket means, two holes in said mounting plate means which are in alignment with said two holes of said bracket means, and screw means extending through said two holes of said mounting plate means and said two holes of said bracket means for securing said mounting plate means on said bracket means with a two-point securement.

15. An assembly according to claim 14; wherein said bracket means includes a first bracket and a second bracket secured to said gas chromatograph on opposite sides of said injection site, said first bracket including a first one of said holes and said second including a second one of said holes.

16. An assembly according to claim 13; wherein said gas chromatograph includes a septum nut assembly at said injection site, said autosamper includes an injector having a base with an opening, and said mounting plate means includes an opening, with said septum nut mating in said opening in said base of said autosampler through said opening in said mounting plate means.

17. An assembly according to claim 13; wherein said mounting plate means includes an opening and a spacer secured to said mounting plate means and extending into said opening, said autosampler includes an injector having a base with spring means for engaging with said spacer through said opening in said mounting plate means to removably secure said injector on said mounting plate means, and said bracket means includes an angled cut-out section in alignment with said spacer to permit access of said spring means under said spacer.

18. An assembly according to claim 17; wherein said bracket means includes a first bracket and a second bracket secured to said gas chromatograph on opposite sides of said injection site, said first bracket including an inner edge facing said injection site and said angled cut-out section extending in said first bracket from said inner edge.

19. An assembly according to claim 13; wherein said mounting plate means includes an arcuate slot, and said autosampler includes an injector having an alignment pin extending into said arcuate slot when said injector is mounted on said mounting plate means.

20. An assembly according to claim 13; wherein said mounting plate means includes a first stabilizing plate secured thereto and depending from the underside thereof, and said bracket means includes a first cut-out section for receiving said first stabilizing plate to stabilize said mounting plate means and said injector on said bracket means.

21. An assembly according to claim 20; wherein said mounting plate means includes a second stabilizing plate secured thereto and depending from the underside thereof, and said bracket means includes a second cut-out section for receiving said second stabilizing plate to stabilize said mounting plate means and said injector on said bracket means.

22. An assembly according to claim 21; wherein said bracket means includes a first bracket and a second bracket secured to said gas chromatograph on opposite sides of said injection site, said first bracket including said first cut-out section and said second bracket including said second cut-out section.

23. An assembly according to claim 13; wherein said bracket means includes a first bracket and a second bracket secured to said gas chromatograph on opposite sides of said injection site.

24. An assembly according to claim 13; wherein said autosampler includes an injector, tray means for holding a plurality of samples and conduit means for connecting the samples to the injector; and said mounting plate means includes horizontal mounting plate section means for securing said mounting plate means to said bracket means and for holding said injector thereon, horizontal securing plate section means for holding said tray means thereon, and vertical plate section means for connecting said horizontal mounting plate section means with said horizontal securing plate section means.

25. An assembly for coupling an autosampler to a gas chromatograph having an injection site, said gas chromatograph including a septum nut assembly at said injection site, said autosampler including an injector having a base with an opening, spring means extending from said base and an injector pin extending from said base, said assembly comprising:
mounting plate means for holding said autosampler, said mounting plate means including:
a first opening for permitting said septum nut to mate in said opening in said base of said autosampler;
a second opening;
a spacer secured to said mounting plate means and extending into said second opening;
an arcuate slot for receiving said injector pin when said injector is mounted on said mounting plate means;
a first stabilizing plate depending from the underside of said mounting plate means;
a second stabilizing plate depending from the underside of said mounting plate means;
bracket means for mounting said mounting plate means to said gas chromatograph, said bracket means being secured to said gas chromatograph adjacent said injection site so as to permit access to said injection site by said autosampler, said bracket means including:
a first bracket secured to said gas chromatograph on one side injection site, said first bracket including:
an inner edge facing said injection site;

an angled cut-out section in alignment with said spacer and extending from said inner edge, so as to permit access of said spring means through said second hole of said mounting plate means and about said spacer to thereby removably secure said injector on said mounting plate means;

a first cut-out section for receivintg said first stabilizing plate to stabilize said mounting plate means and said injector on said bracket means;

a second bracket secured to said gas chromatograph on an opposite side of said injection site, said second bracket including:

an inner edge facing said injection site;

a second cut-out section for receiving said second stabilizing plate to stabilize said mounting plate means and said injector on said bracket means; and securement means for securing said mounting plate means on said bracket means, said securement means including:

a first hole in said first bracket;

a second hole in said second bracket;

a third hole in said mounting plate means in alignment with said first hole when said mounting plate means is positioned on said bracket means;

a fourth hole in said mounting plate means in alignment with said third hole when said mounting plate means is positioned on said bracket means;

a first securing screw extending through said first and third holes; and a second securing screw extending through said second and third holes, wherein said first and second securing screws secure said mounting plate means on said bracket means with a two-point securement.

* * * * *